United States Patent
Popovic

(10) Patent No.: US 11,022,433 B2
(45) Date of Patent: Jun. 1, 2021

(54) LASER ENHANCED RECONSTRUCTION OF 3D SURFACE

(75) Inventor: Aleksandra Popovic, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 463 days.

(21) Appl. No.: 13/577,456

(22) PCT Filed: Jan. 14, 2011

(86) PCT No.: PCT/IB2011/050171
§ 371 (c)(1),
(2), (4) Date: Aug. 7, 2012

(87) PCT Pub. No.: WO2011/098927
PCT Pub. Date: Aug. 18, 2011

(65) Prior Publication Data
US 2012/0310098 A1    Dec. 6, 2012

Related U.S. Application Data

(60) Provisional application No. 61/303,702, filed on Feb. 12, 2010.

(51) Int. Cl.
*G01B 11/25* (2006.01)
*A61B 1/00* (2006.01)
(Continued)

(52) U.S. Cl.
CPC ...... *G01B 11/2513* (2013.01); *A61B 1/00009* (2013.01); *A61B 5/1076* (2013.01);
(Continued)

(58) Field of Classification Search
CPC ..... G01B 11/24; G01B 11/25; G01B 11/2513; G05B 2219/40; G06T 15/06
(Continued)

(56) References Cited

U.S. PATENT DOCUMENTS 5,513,276 A * 4/1996 Theodoracatos ............. 382/154
5,933,223 A * 8/1999 Flock et al. ................... 356/18
(Continued)

FOREIGN PATENT DOCUMENTS

CN   1975323 A   6/2007
CN   101264002 A   9/2008
(Continued)

OTHER PUBLICATIONS

M Hayashibe, N Suzuki, Y Nakamura, "Laser-scan endoscope system for intraoperative geometry acquisition and surgical robot safety management", 2006, Medical Image Analysis, vol. 10, pp. 509-519.*

(Continued)

*Primary Examiner* — James M Kish

(57) ABSTRACT

A method for reconstructing a surface of a three-dimensional object involves a projection of a laser spot pattern onto the surface of the three-dimensional object by a laser, and a generation of a series of endoscopic images as an endoscope is translated and/or rotated relative to the three-dimensional object. Each endoscopic image illustrates a different view of a laser spot array within the laser spot pattern as projected onto the surface of the three-dimensional object by the laser. The laser spot array may be identical to or a subset of the laser spot pattern. The method further involves a reconstruction of the surface of the three-dimensional object from a correspondence of the different views of the laser spot array as illustrated in the endoscopic images.

20 Claims, 4 Drawing Sheets

(51) Int. Cl.
*A61B 5/107* (2006.01)
*G06T 7/521* (2017.01)
*G06T 7/80* (2017.01)
*G06T 7/37* (2017.01)
*A61B 1/317* (2006.01)
*A61B 1/267* (2006.01)
*A61B 1/313* (2006.01)
*A61B 1/04* (2006.01)
*A61B 5/00* (2006.01)
*G06T 7/00* (2017.01)

(52) U.S. Cl.
CPC .............. *A61B 5/1077* (2013.01); *G06T 7/37* (2017.01); *G06T 7/521* (2017.01); *G06T 7/80* (2017.01); *A61B 1/04* (2013.01); *A61B 1/2676* (2013.01); *A61B 1/317* (2013.01); *A61B 1/3132* (2013.01); *A61B 5/4528* (2013.01); *G06T 7/97* (2017.01); *G06T 2200/08* (2013.01); *G06T 2207/10068* (2013.01); *G06T 2207/30004* (2013.01)

(58) Field of Classification Search
USPC ........................................................ 600/476
See application file for complete search history.

(56) References Cited

U.S. PATENT DOCUMENTS

| | | | |
|---|---|---|---|
| 6,503,195 B1 | 1/2003 | Keller et al. | |
| 6,511,418 B2* | 1/2003 | Shahidi et al. | 600/117 |
| 6,945,930 B2* | 9/2005 | Yokota | 600/118 |
| 7,486,805 B2* | 2/2009 | Krattiger | A61B 1/042 |
| | | | 356/603 |
| 8,243,123 B1* | 8/2012 | Geshwind et al. | 348/42 |
| 2003/0123707 A1 | 7/2003 | Park | |
| 2003/0164952 A1* | 9/2003 | Deichmann | A61B 1/05 |
| | | | 356/603 |
| 2005/0107808 A1* | 5/2005 | Evans et al. | 606/139 |
| 2006/0055942 A1 | 3/2006 | Krattiger | |
| 2006/0106283 A1* | 5/2006 | Wallace | A61B 1/00096 |
| | | | 600/109 |
| 2007/0161854 A1 | 7/2007 | Alamaro et al. | |
| 2008/0165360 A1 | 7/2008 | Johnston | |
| 2009/0097039 A1* | 4/2009 | Kawasaki | G01B 11/2509 |
| | | | 356/603 |
| 2009/0244260 A1* | 10/2009 | Takahashi | A61B 1/00172 |
| | | | 348/45 |
| 2010/0020201 A1* | 1/2010 | Chao | G06T 3/4038 |
| | | | 348/239 |
| 2010/0149315 A1* | 6/2010 | Qu | A61B 1/00193 |
| | | | 348/46 |
| 2012/0140243 A1* | 6/2012 | Colonna de Lega | A61F 9/00836 |
| | | | 356/609 |

FOREIGN PATENT DOCUMENTS

| | | |
|---|---|---|
| CN | 101288105 A | 10/2008 |
| GB | 2269453 A | 2/1994 |
| JP | 7260446 A | 10/1995 |
| JP | 2005003367 A | 1/2005 |
| WO | 2004076970 A | 9/2004 |
| WO | 2007080563 A2 | 7/2007 |
| WO | WO 2008066911 A2 * | 6/2008 |

OTHER PUBLICATIONS

Fleig et al., "Surface reconstruction of the surgical field from stereoscopic microscope views of neurosurgery", International Congress Series 1230 (2001), pp. 268-274. (Year: 2001).*

Tola, Engin, "Multiview 3D Reconstruction of a Scene Containing Independently Moving Objects", Middle East Technical University Thesis, 167 pages. (Year: 2005).*

Wurzbacher et al., "Calibration of laryngeal endoscopic high-speed image sequences by an automated detection of parallel laser line projections", Medical IMage Analysis 12 (2008), pp. 300-317. (Year: 2008).*

* cited by examiner

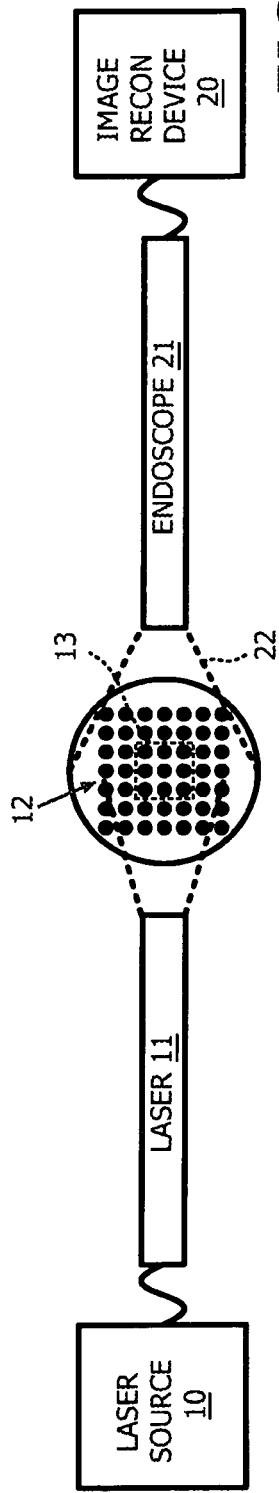
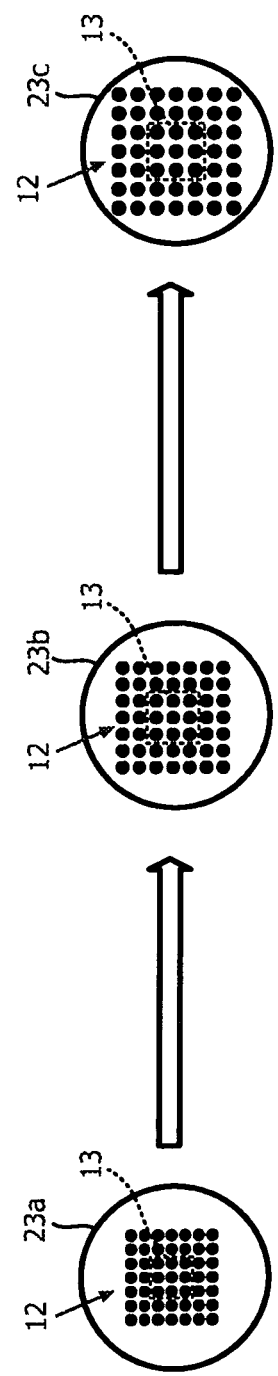
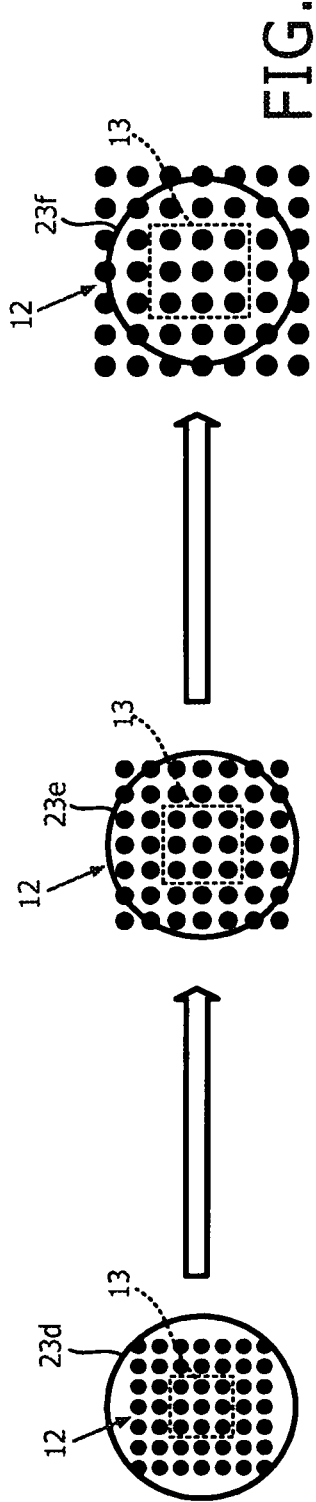

LASER ENHANCED RECONSTRUCTION OF 3D SURFACE

The present invention generally relates to a reconstruction of a three-dimensional ("3D") surface of an object during a minimally invasive endoscopic surgery. The present invention specifically relates to a generation, detection, and utilization of reproducible and precise features of a laser spot pattern on a surface of an object for intra-operative camera calibration of an endoscope and for 3D reconstruction of the surface of the object.

Minimally invasive endoscopic surgery is a surgical procedure in which a rigid or flexible endoscope is introduced into a patient's body through a natural orifice or a small incision in the skin (i.e., a port). Additional surgical tools are introduced into the patient's body through similar ports with the endoscope being used to provide a visual feedback to a surgeon of the surgical tools as related to the surgical site. Examples of minimally invasive endoscopic surgery include, but are not limited to, an endoscopic heart surgery (e.g., an endoscopic cardiac bypass or a mitral valve replacement), a laparascopy for the abdomen, arthroscopy for joints, and bronchoscopy for the lungs.

Laser metrology in endoscopy is a class of methods providing a possibility to measure size of objects in the endoscopy images. It is usually done for industrial endoscopy, but it is also used in medicine. In laser metrology, a collimated laser beam is positioned parallel to the optical axis of the endoscopic camera. The laser beam projects a laser dot on the object or near the object under consideration. Due to the beam collimation of the laser, the size of the dot on or nearby the object remains the same independent of a distance to the object. Thus, the dot size serves as a size calibrator for the image.

One known method in the art places a laser-generating device on the distal end of the endoscope to generate a calibrated laser dot for laser metrology. Basically, this laser metrology method projects one (1) collimated laser dot on the object (e.g., tissue) and retrieves a scale of the object from a diameter of the laser dot.

By comparison, another known method in the art utilizes an endoscope with four laser beams set parallel to the optical axis of an endoscopic camera to project four (4) laser dots on the object (e.g., tissue) to find scale of the object in the image. For this method, radial distortion compensation is performed using a chessboard-like calibration grid to obtain distortion parameters. Subsequently, 3D position of laser dots may be computed from geometrical relations between the points using lens geometry. Finally, calibration rulers are displayed on the endoscopic images.

As previously stated herein for minimally invasive endoscopic surgeries, endoscopes are providing the only visual feedback of the operating site. However, endoscopic images are usually two-dimensional ("2D"), which poses difficulties in obtaining depth information as well as a relative position and size of the objects in the view. Known algorithms for reconstruction of 3D surfaces from a series of 2D images rely on finding correspondence between points in two or more frames. The quality of 3D reconstruction from such algorithms depends heavily on the accuracy of the matched features. In particular, in order to reconstruct 3D surface from 2D+t series, using RANdom SAmple Consensus ("RANSAC") optimization eight (8) or more feature-matches have to be found. However, in surgery, objects in the endoscope view are very often smooth and featureless (e.g., cardiac tissue in cardiac endoscopy or bone surface in arthroscopy), which makes feature detection and matching a difficult task.

The aforementioned laser metrology methods solve the scale problem (i.e., object size) by using a single collimated laser dot or multiple laser beams positioned parallel to the optical axis of the scope. However, these methods do not address the quality issue of 3D reconstruction. Another downside of these methods is that they require the laser beam to be parallel to the optical axis of the endoscope. Thus, the laser source and endoscopic fibers have to be integrated into endoscope itself, which increases the diameter of the endoscope, this increasing invasiveness of the surgical procedure.

The present invention utilizes a laser for projecting a laser spot pattern (e.g., a matrix of circular dots on a surface of a 3D object (e.g., an organ or a tissue of interest) to facilitate a precise reconstruction of the surface of the object and an intra-operative camera calibration that overcomes the difficulties from a 2D endoscopic view in obtaining depth information as well as relative position and size of the surface of the object.

One form of the present invention is a system employing a laser, an endoscope and an image reconstruction device. In operation, the laser projects a laser spot pattern (e.g., a matrix of circular dots) onto a surface of a 3D object (e.g., an organ or tissue of interest). The endoscope generates a series of endoscopic images as the endoscope is translated and/or rotated relative to the 3D object with each endoscopic image illustrating a different view of a laser spot array within the laser spot pattern as projected onto the surface of the 3D object by the laser. The image reconstruction device reconstructs the surface of the 3D object from a correspondence of the differing views of the laser spot array as illustrated in the endoscopic images.

For purposes of the present invention, the term "laser spot pattern" is broadly defined herein as any spatial arrangement of two or more laser spots of any geometrical form, of any color and of any practical dimensions for an endoscopic application, and the term "laser spot array" is broadly define herein as having the spatial arrangement of laser spots of an associated laser spot pattern or any subset thereof. Within a laser spot pattern and a laser spot array, the geometrical form, color and dimension of each spot may be identical or vary among some or all of the laser spots. Additionally, the laser spot array may be pre-operatively or intra-operatively defined within the laser spot pattern.

Furthermore, the term "endoscope" is broadly defined herein as any device having the ability to image from inside a body. Examples of an endoscope for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, or miniaturized (e.g. CCD based) imaging systems.

The foregoing form and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

FIG. 1 illustrates an exemplary embodiment of a 3D image reconstruction system in accordance with the present invention.

FIG. 2 illustrates one exemplary series of different views of a laser spot array in accordance with the present invention.

FIG. 3 illustrates another exemplary series of different views of the laser spot array shown in FIG. 2 in accordance with the present invention.

Figure 4:
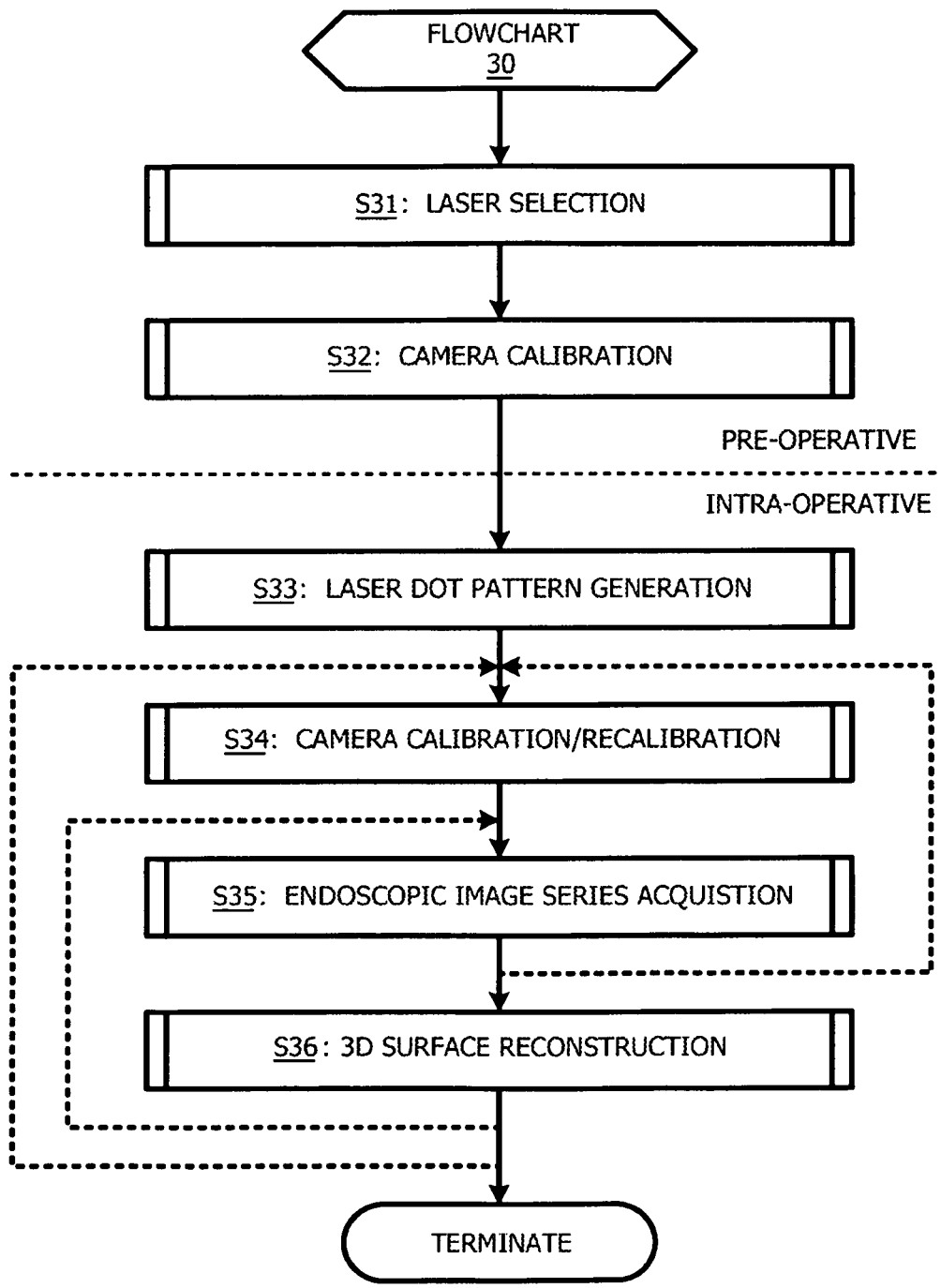
FIG. 4 illustrates a flowchart representative of an exemplary embodiment of an endoscopic surgical method in accordance with the present invention.

An implementation of 3D surface reconstruction algorithms by the present invention is accomplished by a laser projecting a laser spot pattern on a 3D object and an endoscope generating a series of 2D endoscopic images of a laser spot array within the laser spot pattern. The laser spot pattern serves as a reproducible and precise feature as projected on the 3D object to facilitate a correspondence of the laser spot array among the endoscopic images.

For example, as shown in FIG. 1, a laser 11 powered by a laser source 10 projects a laser spot pattern 12 having a 7×7 matrix arrangement of circular dots. Within laser spot pattern 12 is a laser spot array 13 having a 3×3 matrix arrangement of circular dots. During a minimally invasive endoscopic surgery, an endoscope 21 is focused on an entirety or a portion of laser spot pattern 12 whereby a field of view 22 of endoscope 21 encircles laser spot array 13.

More particularly, FIG. 2 illustrates a sequence of endoscopic views 23a-23c generated by endoscope 21 as endoscope 21 is translated in a direction of the 3D object. As such, laser spot pattern 12 enlarges in the different endoscopic views 23a-23c with laser spot array 13 being identifiable in each endoscopic view 23a-23c. The enlargement of laser spot pattern across endoscopic view 23a-23c serves as a motion of laser spot array 13 for purposes of implementing the 3D surface reconstruction algorithms as will be further explained herein. FIG. 3 illustrates an additional sequencing of endoscopic views 23d-23f generated by endoscope 21 as endoscope 21 is further translated in a direction of the 3D object. Again, laser spot pattern 12 enlarges across the endoscopic views 23d-23f with laser spot array 13 being identifiable in each endoscopic view 23d-23f, and the enlargement of laser spot pattern across endoscopic views 23d-23f serves as a motion of laser spot array 13 for purposes of implementing the 3D surface reconstruction algorithms as will be further explained herein.

FIGS. 2 and 3 are provided to emphasize the inventive principle of a laser spot pattern as a reproducible and precise feature as projected on a 3D object to facilitate a correspondence of a laser spot array among the endoscopic images. In practice, preferably the laser spot pattern includes nine (9) or more laser spots, the number of endoscopic images is two (2) or more, and the distance between the endoscopic camera and the laser spot pattern facilitates an identification of the entire laser spot pattern across all of the endoscopic images whereby the laser spot pattern itself serves as the laser spot array. Nonetheless, FIGS. 2 and 3 highlight that a laser spot array, whether an entirety or a portion of the laser spot pattern, must be identifiable among all of the endoscopic images.

Referring back to FIG. 1, an image reconstruction device 20 processes the generated images of the laser spot array to reconstruct a 3D image of the surface of the object. For purposes of the present invention, an image reconstruction device is broadly defined herein as any device structurally configured for generating a 3D reconstruction of a surface of an object by processing endoscopic images in accordance with 3D reconstruction algorithms (e.g., a programmed computer), and the term "generating" as used herein is broadly defined to encompass any technique presently or subsequently known in the art for creating, computing, supplying, furnishing, obtaining, producing, forming, developing, evolving, modifying, transforming, altering or otherwise making available information (e.g., data, text, images, voice and video) for computer processing and memory storage/retrieval purposes, particularly image datasets and video frames.

FIG. 4 illustrates a flowchart 30 representative of an endoscopic surgical method of the present invention. Flowchart 30 includes pre-operative stages S32 and S33, and intra-operative stages S34-S37. The term "pre-operative" as used herein is broadly defined to describe any activity occurring or related to a period or preparations before an endoscopic application and the term "intra-operative" as used herein is broadly defined to describe as any activity occurring, carried out, or encountered in the course of an endoscopic application (e.g., operating the endoscope). Examples of an endoscopic application include, but are not limited to, an arthroscopy, a bronchoscopy, a colonscopy, a laparoscopy, a brain endoscopy, and an endoscopic cardiac surgery. Examples of an endoscopic cardiac surgery include, but are not limited to, endoscopic coronary artery bypass, endoscopic mitral and aortic valve repair and replacement.

Pre-operative stage S31 encompasses a selection of a laser for projecting the laser spot pattern on the 3D object. In practice, a Lasiris™ SNF laser may be used for endoscopic applications whereby the laser has a wavelength approximately 600 nm and a power less than 100 mW. Further, the laser preferably projects laser spot pattern a green or blue 7×7 matrix of circular dots whereby eight (8) or more of the circular dots may serve as the laser spot array. Further, the circular dots may have a 0.5 mm diameter with a 4 mm spacing between the circular dots. To specify a fan angle (FA) of ninety (90) degrees or less, an object size (L) and an operating distance (D) must be know in accordance with the following equation [1]:

$$FA=2*\arcsin(L/(2*D)) \quad [1]$$

Figure 5:
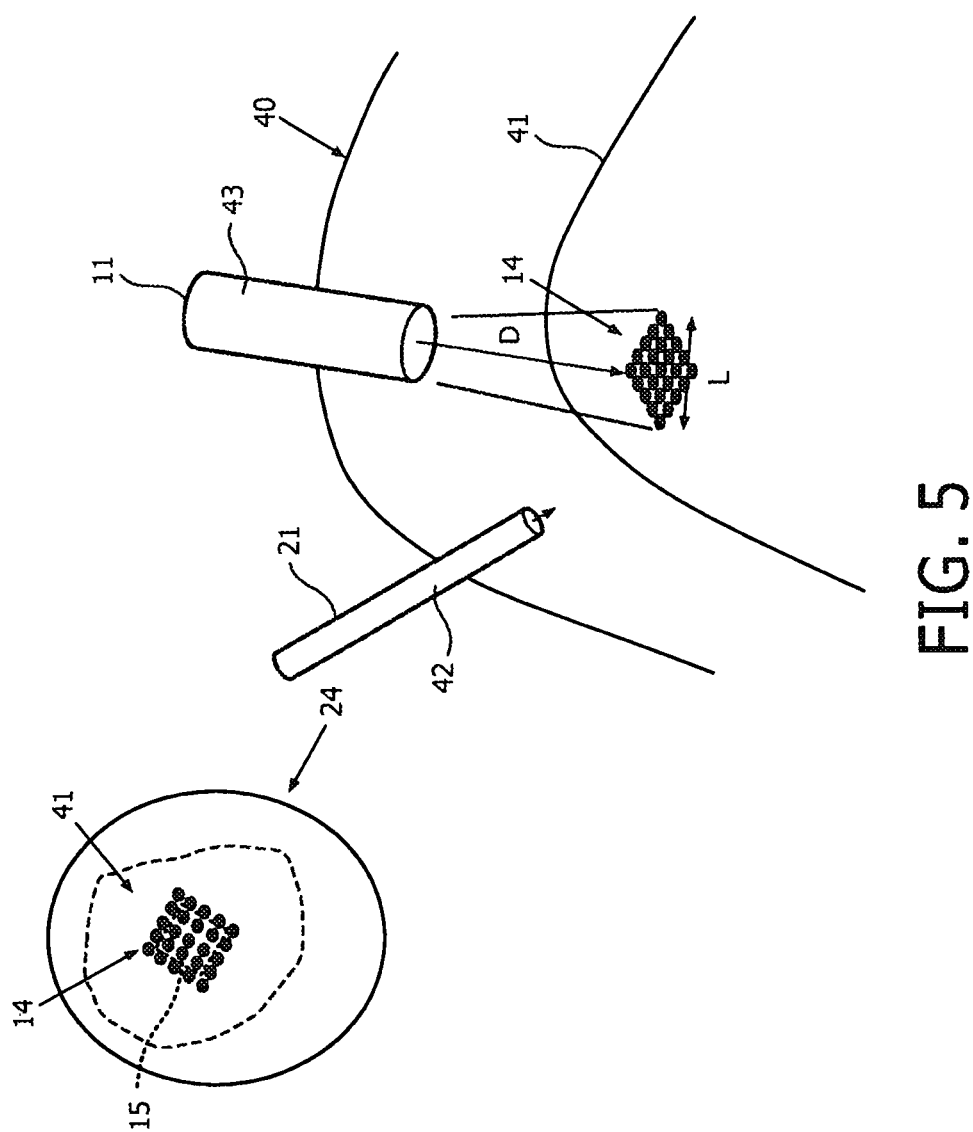
FIG. 5 illustrates an exemplary endoscopic application of the method shown in FIG. 4 by the system shown in FIG. 1.

FIG. 5 illustrates an example of an arthroscopic application involving laser 11 being a distance D from tissue 41 of a knee 40 with an object size L.

Referring again to FIG. 4, pre-operative stage S32 encompasses a known camera calibration of the endoscope. In one embodiment, the laser projects the laser spot pattern on a contrasting planar surface (e.g., a white planar surface) with the laser spot pattern having a uniform matrix (e.g., 7×7 matrix of circular dots) or a matrix with different number of laser spots in the two dimensions (e.g., 6×7 matrix of circular dots). The calibration parameters as well as radial distortion are estimated by the acquiring of images of the laser spot pattern on the planar surface under two (2) or more different orientations of the endoscope relative to the planar surface, and by a detection of the laser points in the images.

Intra-operative stage S33 encompasses a generation of the laser spot pattern on the surface of the 3D object. For example, as shown in FIG. 5, laser 11 is inserted within a surgical instrument port 43 of knee 40 to thereby project a laser spot pattern 14 of a 5×5 matrix of circular dots onto tissue 41.

An execution of intra-operative stage S34 is dependent of whether stage S32 was not executed during the pre-operative phase, or if a re-calibration of the endoscope is required. If executed, intra-operative stage S32 encompasses an endoscope taking images of the laser spot pattern projected onto the 3D object under two (2) or more different orientations of the endoscope relative to the laser spot pattern. For example, as shown in FIG. 5, an endoscope 21 is inserted in a visual port 42 of knee 40 to thereby generate an image of laser spot pattern 14 (e.g., an image 24). The endoscope 24 can be moved around port 42 (i.e., a pivot point) at any direction and rotation to generate images of the same laser spot array from different viewing angles and directions. Thereafter, a detection of the laser spot pattern 14 as the laser spot array within the images or a detection of a laser spot array 15 within the images would enable an estimation of the camera parameters.

Detection of laser spots can be performed with any algorithm known in art, such as color thresholding. Result of the detection is $x=[x,y]^T$ position of the spot in a coordinate system of each image.

Intra-operative stage S35 encompasses a generation of a series of two (2) or more images of the laser spot pattern on the 3D object as the endoscope is translated and/or rotated relative to the 3D object and the port 42. For example, as shown in FIG. 5, endoscope 21 is inserted in port 42 of knee 40 to thereby generate images of laser spot pattern 14 (e.g., an image 24) as endoscope 21 is translated in a direction of tissue 41 as shown by the arrow.

Intra-operative stage S36 encompasses a 3D reconstruction of the surface of the object from the endoscopic images acquired during stage S35 and the calibration of the endoscope obtained during pre-operative stage S32 or intra-operative stage S34. In practice, any 3D reconstruction algorithm may be implemented during stage S36 to achieve the 3D reconstruction of the object. In one embodiment, a shown in FIG. 6, a flowchart 50 representative of a 3D surface reconstruction that may be implemented during stage S36.

Figure 6:
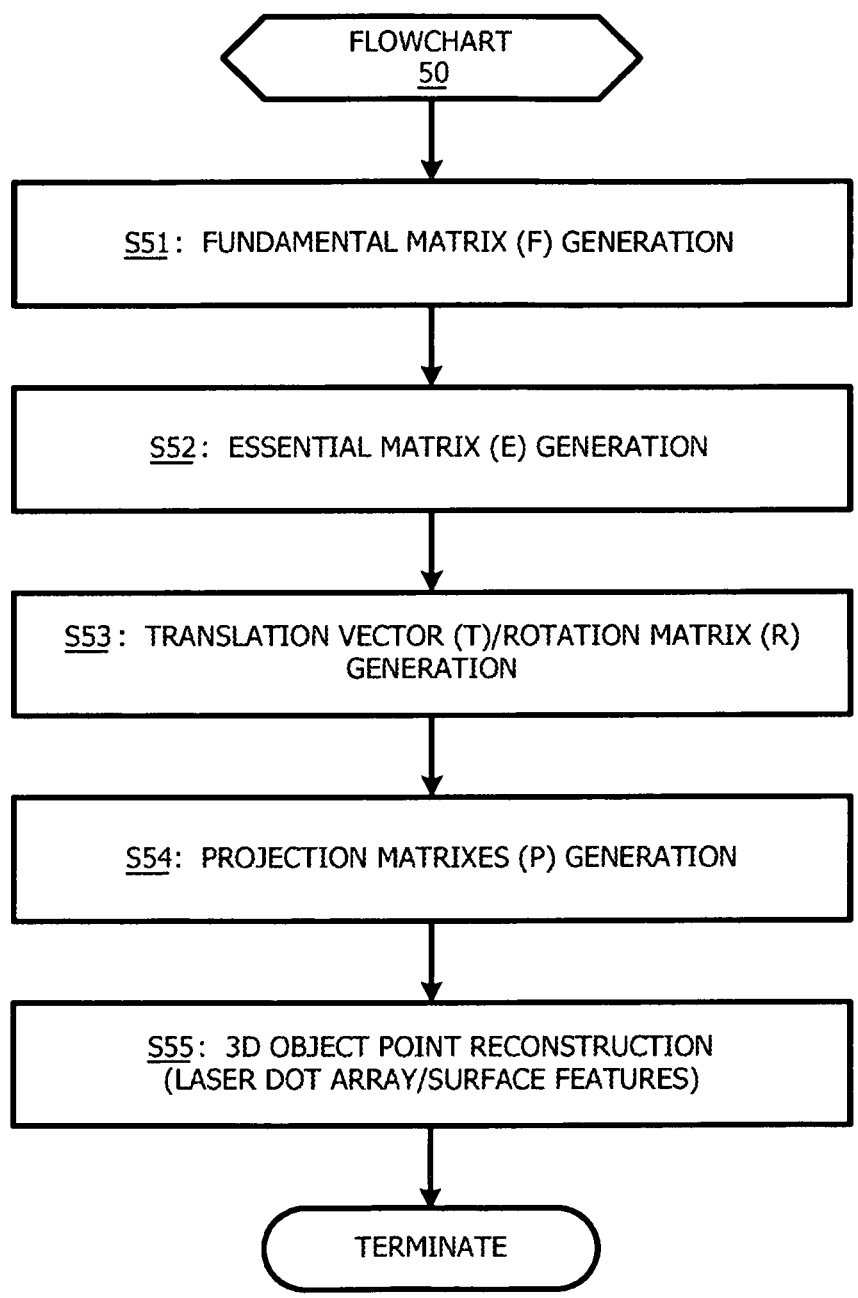
FIG. 6 illustrates a flowchart representative of an exemplary embodiment of a 3D surface reconstruction method in accordance with the present invention.

Referring to FIG. 6, a stage S51 of flowchart 50 encompasses a generation of a fundamental matrix (F) for relating the different views of the laser spot array across the endoscopic mages. In one embodiment, for the same laser spot in two different views (x) and (x'), fundamental matrix (F) is a 3×3 matrix and is defined in accordance with the following known equation [2]:

$$x^T*F*x'=0 \qquad [2]$$

For N laser spots in two different views, a set of N equations is defined:

$$x_1^T*F*x_1'=0 \qquad [3]$$
$$\ldots$$
$$x_N^T*F*x_N'=0$$

The unknown (F) from equations [3] may be computed using an Eight-point algorithm if the laser spot array has eight (8) laser spots (N=8), or may be computed using an iterative method (e.g., RANSAC) if the laser spot array includes nine (9) or more laser spot.

Stage S52 encompasses a generation of an essential matrix (E) or relating the different views of the laser spot array across the endoscopic mages. In one embodiment, the essential matrix (E) is computed from the following known equation [4]:

$$E=K^T*F*K=0 \qquad [4]$$

Calibration matrix (K) is a 3×3 matrix representative of the pre-operative or intra-operative calibration of the endoscope.

Stage S53 encompasses a generation of a translation vector (T) and a rotation matrix (R) (if the endoscope was rotated) as a function of the essential matrix (E). In one embodiment, a translation vector (T) and a rotation matrix (R) are derived from the following known equation [5]:

$$E=U*\Sigma*V^T=0 \qquad [5]$$

Stage S54 encompasses a generation of a projection matrix for each view of the laser spot array. In one embodiment for two (2) views of the laser spot array, a projection matrix $P_1$ for a view associated with spots (x) and a projection matrix $P_1$ for a view associated for spots (x') are computed from the following known equations [6] and [7]:

$$P_1=K*[I|0] \qquad [6]$$

$$P_2=K^T*[R|T]*K \qquad [7]$$

Stage S55 encompasses a 3D object point reconstruction from the laser spot array or salient features of the object (e.g., edges) in the endoscopic images. In one embodiment, using a pinhole camera model for two (2) views, a 3D object point X is computed from the following known equations [8] and [9]:

$$x=P_1*X \qquad [8]$$

$$x'=P_2*X \qquad [9]$$

The computed 3D object point X may be reconstructed using triangulation and equations [8] and [9].

For points x and x', two sets could be used for stage S55.

In a first embodiment, laser spots x and x' can be used as features. These are strong features, because they are highly precise and reliable. This embodiment would result in a very sparse 3D model having as many points as the associated laser spot array.

In second embodiment, weak object surface features (e.g., edges) detected using feature detection methods known in art (e.g., a SIFT method) may be used with projection matrixes $P_1$ and $P_2$ computed from points x and x'. This method would result in a dense surface with lower precision of points x and x', but maintaining high precision of projection matrixes $P_1$ and $P_2$.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A system comprising:
a laser configured to project a spot array defined within a projected spot pattern onto corresponding surface portions of a surface of a three-dimensional object;
an endoscope configured to be translated and/or rotated relative to the three-dimensional object to generate a plurality of 2D images each illustrating at least one of a different viewing angle and direction relative to the projected spot array within the projected spot pattern as projected onto the corresponding surface portions of the three-dimensional object by the laser and being further configured to ensure that the entire projected spot array projected on the corresponding surface portions of the three-dimensional object is visible in each of the plurality of 2D images and configured to ensure that a distance between the endoscope and the three-dimensional object changes between each of the plurality of 2D images relative to the corresponding surface portions of the three-dimensional object that the projected spot array is projected onto; and
an image processing device in communication with the endoscope and configured to reconstruct a 3D image of the surface of the three-dimensional object from a correspondence of differing views of the spot array between each of the generated plurality of 2D images, wherein the image processing device is configured to reconstruct the 3D image of the surface of the three-dimensional object using coordinates that only include 2D coordinates from each of the generated plurality of 2D images that are each captured at different distances between the endoscope and the three-dimensional object.

2. The system of claim 1, wherein the projected spot array includes all of the projected spot pattern.

3. The system of claim 1, wherein the projected spot array on the corresponding surface portions of the three-dimensional object is a subset of the projected spot pattern.

4. The system of claim 1, wherein the device is further configured to
generate a fundamental matrix for relating the different viewing angles and/or directions of the projected spot array on the corresponding surface portions of the three-dimensional object in the generated plurality of 2D images; and
reconstruct points on the three-dimensional object as a function of the fundamental matrix and the correspondence between the different viewing angles and/or directions of the projected spot array on the corresponding surface portions of the three-dimensional object.

5. The system of claim 1, wherein the device is further configured to
generate a fundamental matrix for relating the different viewing angles and/or directions of the projected spot array on the corresponding surface portions of the three-dimensional object in the generated plurality of 2D images;
detect surface features of the object from the generated plurality of 2D images; and
reconstruct points on the three-dimensional object as a function of the fundamental matrix and the surface features of the object detected in the generated plurality of 2D images.

6. The system of claim 1, wherein the device is further configured to generate a fundamental matrix for relating the different viewing angles and/or directions of the projected spot array on the corresponding surface portions of the three-dimensional object in the generated plurality of 2D images.

7. The system of claim 6, wherein the endoscope includes a camera, and the device is further configured to generate an essential matrix for relating the different viewing angles and/or directions of the projected spot array on the corresponding surface portions of the three-dimensional object in the generated plurality of 2D images, the essential matrix being a function of the fundamental matrix and a calibration matrix associated with calibration of the camera.

8. The system of claim 7, wherein the device is further configured to generate a translation vector and a rotation matrix as a function of the essential matrix.

9. The system of claim 8, wherein the device is further configured to generate a projection matrix for each of the different viewing angles and/or directions of the projected spot array on the corresponding surface portions of the three-dimensional object in the generated plurality of 2D images as a function of the translation vector and the rotation matrix, each projection matrix being a linear transformation of an associated view of the projected spot array in one of the generated plurality of 2D images.

10. The system of claim 9, wherein the device is further configured to reconstruct points on the three-dimensional object as a function of each projection matrix and the associated different viewing angles and/or directions of the projected spot array on the corresponding surface portions of the three-dimensional object from the generated plurality of 2D images.

11. The system of claim 9, wherein the device is further configured to
detect surface features of the object in the generated plurality of 2D images for each view of the different viewing angles and/or directions of the projected spot array on the corresponding surface portions of the three-dimensional object; and
reconstruct points on the three-dimensional object as a function of each projection matrix and each surface feature of the object detected in the different viewing angles and/or directions in the generated plurality of 2D images.

12. The system of claim 1, wherein the endoscope is intra-operatively calibrated from at least two of the plurality of 2D images.

13. A system comprising:
an endoscope configured to be translated and/or rotated relative to a three-dimensional object to generate a plurality of 2D images each illustrating at least one of a different viewing angle and direction of a spot array included within a spot pattern as projected onto corresponding surface portions of the three-dimensional object and being further configured to ensure that the entire projected spot array projected on the corresponding surface portions of the three-dimensional object is visible in each of the plurality of 2D images and configured to ensure that a distance between the endoscope and the three-dimensional object changes between each of the plurality of 2D images relative to the corresponding surface portions of the three-dimensional object that the spot array is projected onto; and
an image processing device in communication with the endoscope and configured to reconstruct a 3D image of the surface of the three-dimensional object from a correspondence of differing views of the spot array between each of the plurality of 2D images, wherein the image processing device is configured to reconstruct the 3D image of the surface of the three-dimensional object using coordinates that only include 2D coordinates from each of the generated plurality of 2D images that are each captured at different distances between the endoscope and the three-dimensional object.

14. The system of claim 13, wherein the device is further configured to
generate a fundamental matrix for relating the different viewing angles and/or directions of the projected spot array on the corresponding surface portions of the three-dimensional object in the generated plurality of 2D images; and
reconstruct points on the three-dimensional object as a function of the fundamental matrix and the different viewing angles and/or directions of the projected spot array on the corresponding surface portions of the three-dimensional object.

15. The system of claim 13, wherein the device is further configured to
generate a fundamental matrix for relating the different viewing angles and/or directions of the projected spot array on the corresponding surface portions of the three-dimensional object in the generated plurality of 2D images;
detect surface features of the object in the generated plurality of 2D images; and
reconstruct points on the three-dimensional object as a function of the fundamental matrix and the surface features of the object detected in the generated plurality of 2D images.

16. A method for reconstructing a surface of a three-dimensional object, the method comprising:
projecting a spot array defined within a projected spot pattern onto corresponding surface portions of the surface of the three-dimensional object;
generating with an endoscope a plurality of 2D images each illustrating at least one of a different viewing angle and direction relative to the spot array within the spot pattern as projected onto the corresponding surface portions of the three-dimensional object as the endoscope is translated and/or rotated relative to the three-dimensional object;
ensuring that the entire spot array projected on the corresponding surface portions of the three-dimensional object is visible in each of the plurality of 2D images while ensuring that a distance between the endoscope and the three-dimensional object changes between each of the plurality of 2D images relative to the corresponding surface portions of the three-dimensional object that the spot array is projected onto; and
reconstructing a 3D image of the surface of the three-dimensional object from a correspondence of differing views of the spot array between each of the generated plurality of 2D images, wherein reconstructing the 3D image of the surface of the three-dimensional object comprises using coordinates that only include 2D coordinates from each of the generated plurality of 2D images that are each captured at different distances between the endoscope and the three-dimensional object for reconstructing the 3D image.

17. The method of claim 16, wherein the projected spot array on the corresponding surface portions of the three-dimensional object is a subset of the projected spot pattern.

18. The method of claim 16, wherein the endoscope is intra-operatively calibrated from at least two of the plurality of 2D images.

19. The method of claim 16, wherein the reconstructing comprises acts of:
generating a fundamental matrix for relating the different viewing angles and/or directions of the spot array on the corresponding surface portions of the three-dimensional object in the generated plurality of 2D images; and
reconstructing points on the three-dimensional object as a function of the fundamental matrix and the correspondence between the different viewing angles and/or directions of the spot array on the corresponding surface portions of the three-dimensional object.

20. The method of claim 16, wherein the reconstructing comprises acts of:
generating a fundamental matrix for relating the plurality of different viewing angles and/or directions of the spot array on the corresponding surface portions of the three-dimensional object in the generated plurality of 2D images;
detecting surface features of the object in the generated plurality of 2D images; and
reconstructing points on the three-dimensional object as a function of the fundamental matrix and the surface features of the object detected in the generated plurality of 2D images.

* * * * *